United States Patent [19]

Meier et al.

[11] Patent Number: 5,759,567
[45] Date of Patent: Jun. 2, 1998

[54] METHOD OF ALTERING THE CONTENTS OF EGGS

[75] Inventors: Albert H. Meier, Baton Rouge, La.; John M. Wilson, Charlestown, Mass.

[73] Assignee: The Board of Supervisors of Louisiana State University and Agricultural and Mechanical College, Baton Rouge, La.

[21] Appl. No.: 777,463

[22] Filed: Dec. 30, 1996

Related U.S. Application Data

[63] Continuation of Ser. No. 455,390, May 31, 1995, Pat. No. 5,665,375.

[51] Int. Cl.[6] .......................... A61K 9/14; A61K 31/195
[52] U.S. Cl. ..................... 424/439; 424/442; 424/489
[58] Field of Search ............................ 424/439, 442, 424/489; 426/2

[56] References Cited

U.S. PATENT DOCUMENTS

| | | | |
|---|---|---|---|
| 4,241,082 | 12/1980 | Baba | 424/309 |
| 5,091,195 | 2/1992 | Havens | 426/2 |
| 5,106,836 | 4/1992 | Clemens | 514/21 |

FOREIGN PATENT DOCUMENTS 1518726   7/1978   United Kingdom.

OTHER PUBLICATIONS

Shafey, T.M. et al. "Comparison Between Wheat, Triticale, Rye, Soyabean Oil and Strain of Laying Bird on the Production and Cholesterol & Fatty Acid Content of Eggs." British Poultry Science 33:339–346 (1992).

Amer, H.A. et al. "Amino acid pattern of eggs as influenced by supplementation of dopamine agonists and antagonists in laying hens." Die Nahrung 35:203–208 (1991).

Leeson, S. et al. "Response of Laying Hens to Supplemental Niacin" Poultry Science 70:1231–1235 (1991).

Luhman, C.M. et al. "Research Note: The Effect of Feeding Lovostatin and Colestipol on Production and Cholesterol Content of Eggs" Poultry Science 69:852–855 (1990).

Waldroup, P.W. et al. "Influence of Probucol on Egg Yolk Cholesterol Content and Performance of Laying Hens" Poultry Science 65:1949–1954 (1986).

Beyer, R.S. "Efforts to Reduce the Cholesterol Content of Eggs and Poultry Meat" 1991 Georgia Nutrition Conference, Thursday, Nov. 21, 1991, 10:25 A.M. pp. 115–127.

Hocking, P.M. et al. "Plasma Growth Hormone and Insulin–like Growth Factor I (IGF–I) Concentrations at the Onset of Lay in Ad Libitum and Restricted Broiler Feeder Fowl" British Poultry Science 35:299–308 (1994).

Primary Examiner—Thurman K. Page
Assistant Examiner—James M. Spear
Attorney, Agent, or Firm—Darby & Darby

[57] ABSTRACT

A method for reducing the total fat and cholesterol contents and the ratio of saturated to unsaturated fatty acids and for increasing total protein content in eggs produced by animals is described. The level of L-Dihydroxyphenylalanine (L-DOPA) in the bloodstream of the poultry is elevated so as to cause the animals to produce eggs which have a reduced cholesterol content and eggs which have a lower ratio of saturated to unsaturated fatty acids. In a preferred embodiment the L-DOPA is orally administered to poultry by incorporation in the food for said poultry.

23 Claims, No Drawings

METHOD OF ALTERING THE CONTENTS OF EGGS

This is a continuation of application Ser. No. 08/455,390, filed May 31, 1995, U.S. Pat. No. 5,665,375.

FIELD OF THE INVENTION

1. Background of the Invention

This invention relates generally to a method of altering the lipid and protein contents of eggs, and more particularly to a method for reducing the total fat and cholesterol contents, reducing the ratio of saturated to unsaturated fatty acids and for increasing the protein content of eggs and especially poultry eggs.

2. Prior Art

Eggs have been a staple food item on the menu of man for at least as long as recorded history. In addition to being inexpensive, eggs are an excellent source of dietary protein. Recently, however, the egg has come under increasing medical and dietary criticism due to the high level of cholesterol and the high ratio of saturated to unsaturated fatty acids contained within the egg yolk. In general, poultry eggs contain between about 235 mg. and 280 mg. of cholesterol. The ratio of saturated to unsaturated fatty acids in an egg is generally between 0.80 and 0.92. Because the egg, and particularly the poultry egg, is such an inexpensive source of dietary protein, considerable research has been carried out in an effort to develop an egg which has reduced quantities of cholesterol and saturated fats. This research has resulted in several methods for reducing the cholesterol and saturated fatty—acid content of the egg. However, the methods currently in use have generally proved to be unsatisfactory.

It is desirable to reduce the cholesterol content and the ratio of saturated to unsaturated fats in eggs because, for humans, reduction of dietary cholesterol and saturated fat is associated with a decreased risk of contracting certain diseases, including, by way of example, coronary artery disease, atherosclerosis, and stroke. Also, reducing cholesterol and saturated/unsaturated fat ratios can significantly reduce the complications of diabetes.

One currently known method of cholesterol reduction involves chemically separating the cholesterol and/or yolk from the total contents of the egg. This requires breaking the egg shell and then chemically removing the cholesterol. This expensive, labor intensive method results in a liquified egg product that is not altogether satisfactory from the standpoint of appearance and taste.

Another currently used technology involves feeding layer hens diets that are high in fiber and low in saturated fats in an effort to reduce the cholesterol and saturated fatty acid content of the eggs produced by such hens. None of the dietary manipulation methods have been successful in reducing the levels of cholesterol or saturated fat by more than 7% as compared to untreated control animals (Shafey, et al., 1992). Further, the special feed blends that must necessarily be employed in carrying out this method are several times more expensive than the feed materials currently used in commercial layer hen diets.

Dietary supplements of soybean oil (sterols) have had variable success. In one study a 35% decrease in egg cholesterol was reported when hens were fed a 4% sitosterol diet. However, a later study could not replicate the earlier study nor did it find any significant effect of various soybean derived sterols on egg cholesterol levels (Bartov, Barnstein, and Budowski, *Variability of Cholesterol Concentration in Plasma and Egg Yolks of Hens and Evaluation of the Effect of some Dietary Oils*, Poultry Science 50:1357 (1971).

In addition to the above-mentioned methods, several drugs that have been used for the treatment of hypercholesterolemia and hyperlipidemia have been administered to layer hens in an attempt to lower egg cholesterol levels. These have generally been unsuccessful in lowering total egg cholesterol content or in altering the ratio of saturated to unsaturated fats. These drugs include by way of example: Lovastatin, bile-acid binding agents such as Colestipol, and Niacin. At best, an 11–15% reduction in egg cholesterol has been realized with these treatments. However, this modest reduction in cholesterol level is usually accompanied by reduced egg production, feed efficiency, or egg quality (Peeson, et al., 1991; Pubman, et al., 1990; Waldraup, et al., 1986).

To solve the problem efforts have been made to lower the egg cholesterol content by lowering the level of cholesterol in the blood in the layer hen. However, it has been found that the level of cholesterol in an egg is not necessarily related to the level of plasma cholesterol in the animal which produced the egg. In one study, a 50% reduction in plasma cholesterol of layer hen had no effect on total egg cholesterol content (Beyer, *Efforts to Reduce the Cholesterol Content of Eggs and Poultry Meat*, Proc. Georgia Nutrition Conference 1991: 115–127, 1991).

What is desired is a method of causing poultry to lay eggs having a reduced cholesterol content, or to cause poultry to lay eggs having a reduced ratio of saturated to unsaturated fatty acids, or both; without introducing any foreign substances or materials into the eggs. Enhancement of protein content and reduction of total fat content in eggs would also tend to increase the already substantial benefit of egg consumption.

SUMMARY OF THE INVENTION

One object of the present invention is to provide a method for producing eggs having a-reduced cholesterol content.

Another object of the present invention is to provide a method for producing eggs having a reduced ratio of saturated to unsaturated fatty acids.

A still further object of the present invention is to provide a method for producing eggs that have a reduced total fat content.

Another object of the present invention to provide a method for producing eggs with an increased total protein content.

Another object of the present invention is to provide a method of producing poultry eggs having a reduced cholesterol and total fat content as well as a reduced ratio of saturated to unsaturated fatty acids and increased total protein content, and which method does not involve introducing an unnatural substance into the eggs.

A still further object of the present invention is to provide a method for reducing the cholesterol and total fat content, reducing the ratio of saturated to unsaturated fatty acids and for increasing the total protein content in eggs produced by poultry which does not involve altering eggs already produced, but instead involves methods for treating the poultry responsible for egg production prior to the time such poultry lays the eggs.

Accordingly a method for reducing the cholesterol and total fat content, the ratio of saturated to unsaturated fatty acids and for increasing the total protein content in eggs is disclosed herein. The method comprises administering an effective amount of L-dihydroxyphenylalanine (L-DOPA) to said animal for reducing the cholesterol content of eggs produced by said poultry. The method of the invention increases the level of L-DOPA in the bloodstream of the poultry so as to achieve the desired alteration in lipid and protein contents of eggs.

DETAILED DESCRIPTION OF THE PREFERRED EMBODIMENT

Without limiting the scope of the invention, the preferred embodiment of the invention will be set forth.

It has been discovered by the inventors of the present invention that elevating the level of the amino acid L-Dihydroxy-phenylalanine (hereinafter L-DOPA), in the blood stream of poultry, has the effect of reducing the cholesterol content in the eggs produced by such poultry, and also has the effect of reducing the ratio of saturated to unsaturated fatty acids in the eggs produced by such poultry. Further, elevating the level of L-DOPA in the bloodstream of poultry reduces the total fat content and increases the total protein content of the eggs they produce. The amino acid L-DOPA is a natural substance found in humans as well as animals, including poultry.

"L-DOPA," as used herein, is intended to include molecules containing substitutions in the chemical formula of L-DOPA not affecting the chemical activity and efficacy of the L-DOPA molecule in this application.

"An effective amount," as used herein, is intended to mean a quantity of L-DOPA which, when administered to a hen, will cause the eggs produced by that hen to have a noticeable reduction (i.e. at least about 10%) of one or more of the cholesterol content, the total fat content or the ratio of saturated to unsaturated fatty acids, or to have an increased total protein content as compared to eggs from untreated animals. Reduction of the cholesterol and fat contents and a reduction of the ratio of saturated to unsaturated fatty acids as well as increases in total protein are significant benefits to the egg products industry and the egg consuming public.

These effects have been verified in two studies conducted by the applicants. The methodologies and results of these studies are described below.

STUDY ONE

In Study One 24 Leghorn hens were obtained from a commercial private breeder at 17–18 weeks of age. The hens were separated into two groups of 12 hens each and placed on long day lengths (LD 16:8 i.e. 16 hours of light and 8 hours of dark) to stimulate egg products. The first group of hens were fed a Purina Layer Diet 18% protein, 1.5% lipid, 4.5% fiber). The second group of hens were fed the same diet supplemented with L-Dihydroxyphenylalanine (L-DOPA). The L-DOPA was in the form of a powder and was mixed in with the normal diet. 50 mg of L-DOPA per kg of layer hen body weight per day, based on average daily feed consumption, was added to the layer hen's daily diet. Egg production and feed consumption were monitored daily. Eggs were collected and analyzed for cholesterol, fat, protein and fatty acid contents during weeks 6, 8 and 11 of treatment. The eggs collected for analysis were also analyzed for L-DOPA content. The results of the study are quantified in Table 1 below.

TABLE 1

Effects of L-DOPA on Total Cholesterol and Fatty Acid Composition of White Leghorn Eggs

| Cholesterol (mg/Ml) | Fatty Acids (%) | | Ratio (sat/unsat) |
|---|---|---|---|
| | Saturated | Unsaturated | |
| Control 5.3 ± 0.4[1] | 44.8 ± 5.9 | 52.1 ± 7.3 | 0.86 |
| Group Treatment 3.8 ± 0.5[a] | 35.9 ± 8.2 | 60.2 ± 3.7[a] | 0.60 |

Note 1
Mean ± Standard Error of the Mean. No differences in egg L-DOPA content were found between untreated and L-DOPA treated hens.
Note a
Differs significantly from control ($P < 0.05$)

As shown by the results in Table 1, the layer hens receiving the L-DOPA supplemented feed produced eggs having a significantly lower cholesterol content than the eggs of those layer hens receiving the unsupplemented feed (averages of 228 mg. for eggs from treated animals as compared to 318 mg. for eggs from untreated animals. Specifically, the eggs from the treated group of layer hens were 28% lower in cholesterol than the eggs from the control group of layer hens. The elevation of plasma L-DOPA levels which results in cholesterol reductions of 25% and greater is a particularly preferred embodiment. Such reductions are significant not only statistically, but also commercially, because the U.S. Department of Agriculture requires a cholesterol reduction of 25% or more before a product can be labelled as containing "Reduced Cholesterol".

The ratio of saturated to unsaturated fatty Acids was also reduced (30% reduction) in the eggs produced by the layer hens receiving the L-DOPA supplemented feed. This reduction is statistically significant. Another significant finding of Study One was that there was no noticeable difference in the L-DOPA levels between the eggs of either population of layer hens used int he study. Egg production in the treated hens was equal to or better than for the control group.

STUDY TWO

In Study Two 300 White Leghorn layer hens were obtained from a commercial breeder at 19 weeks of age. The hens were separated into four groups of 75 hens each and placed on long day lengths (LD 16:8) to stimulate egg production. The hens in one group, the untreated control group, were fed a layer diet of 17% protein, 3% lipid, 5% crude fiber, and 3.5% calcium. The three other groups were fed the same diet supplemented with L-DOPA. The supplement amounts varied for the three treatment groups: 10 (Group 2), 40 (Group 3), or 100 (Group 4) mg of L-DOPA per kg of layer hen body weight per day for the entire 10 week treatment period (dosage was based on initial body weight and feed consumption measured prior to the start of treatment).

Egg production and feed consumption were monitored daily. The layer hens were weighed before and after the treatment period.

The L-DOPA supplemented diets of Groups 2, 3, and 4 were mixed every four days to circumvent the tendency for L-DOPA in feed to oxidize and degrade over time. Eggs were collected at random from the control and treatment groups during weeks 7 and 10 of treatment for the analysis of total protein, total lipid, cholesterol and fatty acid composition. The results of the study are quantified in Table 2.

TABLE 2

Effects of L-DOPA on Several Components of White Leghorn Eggs

| Total Protein (g/100 ml) | Total Fat (g/100 ml) | Protein/Fat | Cholesterol (mg/ml) | Fatty Acids (%) sat. | Fatty Acids (%) unsat. | Ratio S/U |
|---|---|---|---|---|---|---|
| Control 13.4 ± 0.1[1] | 10.6 ± 0.1 | 1.2 | 4.6 ± 0.2 | 44.7 ± 1.6 | 53.2 ± 2.1 | 0.84 |
| DOPA 13.8 ± 0.1 (10 mg/kgbw/day) | 10.1 ± 0.1 | 1.3 | 4.5 ± 0.3 | 47.1 ± 2.0 | 51.1 ± 2.2 | 0.92 |
| DOPA 17.4 ± 0.2* (40 mg/kgbw/day) | 10.2 ± 0.1 | 1.7 | 4.1 ± 0.2 | 39.9 ± 1.7* | 58.5 ± 19* | 0.68 |
| DOPA 18.9 ± 0.2* (100 mg/kgbw/day) | 8.9 ± 0.1* | 2.1 | 3.5 ± 0.3* | 37.9 ± 1.6* | 61.1 ± 1.8* | 0.63 |

[1]Mean ± Standard Error of Mean; n = 10 or 11 eggs (65 g)/group
*Differs significantly from control (p < 0.05)

Referring to the results in Table 2, it will be seen that the population of laying hens receiving the L-DOPA supplemented feed produced eggs that had a lower cholesterol content than the eggs of those layer hens receiving the unsupplemented feed. The saturated to unsaturated fatty acids ratio was also reduced in the eggs produced by the population of layer hens receiving the L-DOPA supplemented feed (compare control ratio of 0.84 to treated ratio of 0.63 at the highest dosage). The difference in cholesterol level was statistically significant at the 100 mg/kg body weight L-DOPA dosage level and resulted in a cholesterol reduction of 24%. Total fat content was significantly reduced (160% reduction in eggs from hens treated with L-DOPA at a dose of 100 mg/kg body weight). Total egg protein content was significantly increased by both the 40 mg/kg and 100 mg/kg dosage levels (30% and 41%, respectively).

The reduction in the ratio of saturated to unsaturated fats was statistically significant for L-DOPA dosage levels of 40 mg/kg body weight (19% reduction), and 100 mg/kg body weight (25% reduction). The results in both Study One and Study Two were achieved without a reduction in egg production or body weight, nor any change in feed consumption, of the layer hens. Although the study period for Study Two was a total of ten weeks, the eggs collected at week seven, as well as the eggs collected at week ten, displayed reduced cholesterol levels.

The rates at which the L-DOPA can be administered may be varied. Additionally, one skilled in the art can vary the methods of administration. In order to obtain eggs having cholesterol levels that are reduced, on average, by at least 20% as compared to eggs from untreated animals, the animals to be treated should receive an effective amount of L-DOPA to reduce cholesterol of between 40 mg/kg to about 300 mg/kg of body weight of L-DOPA per day. Preferably, the animals to be treated according to the present invention should receive between 50 mg/kg and 150 mg/kg of body weight of L-DOPA per day. The total L-DOPA daily dose can be administered in a single dose or in divided doses. Administration may be via the oral route, by injection, or subcutaneous implant. Preferably, animals treated according to the present invention will ingest L-DOPA in their feed for at least 3 days before eggs exhibiting the reduced cholesterol composition of the present invention are oviposited. The essence of the invention is the discovery that elevating L-DOPA in the bloodstream of poultry has the effect of reducing cholesterol and fat contents and the ratio of saturated to unsaturated fat in the eggs oviposited by the poultry. In the field, in actual service conditions, one skilled in the art can envision several preferred methods by which L-DOPA can be administered to poultry. For example, the L-DOPA may be administered to the poultry by subcutaneous or intraperitoneal injection or by insert of timed-release subcutaneous L-DOPA implants.

Although the L-DOPA in the preceding studies was administered orally with animal feed, the beneficial effects are believed to be derived from an elevated L-DOPA level in the blood of poultry. As an alternative to administering L-DOPA orally to maintain increased levels of L-DOPA in the blood of poultry, drugs which inhibit the degradation of L-DOPA may also be administered and achieve the same effect. Examples of such drugs, known as dopa decarboxylase inhibitors, are carbidopa and benserazide, both of which have been used in conjunction with L-DOPA in the treatment of Parkinson's disease. At least 5 mg/kg preferably between 10 mg/kg and 50 mg/kg of body weight of carbidopa or benserazide per day should be administered to an animal together with the L-DOPA dosages described above. As the quantity of carbidopa or benserazide is increased, the time that the L-DOPA remains at an effective cholesterol lowering concentration in the bloodstream is increased. Accordingly, the quantity of L-DOPA administered to the animal may be decreased to the lower end of the dosage ranges described above when carbidopa or benserazide is also being administered to an egg laying animal in accordance with the present invention.

By using the aforementioned inhibitors, the amount of L-DOPA required to be administered can be reduced or eliminated resulting in a substantial economic savings. Drugs which stimulate L-DOPA synthesis include, but are not limited to, tyrosine and phenylalanine. Inhibitors of the enzyme dopamine beta hydroxylase such as fusaric acid, disulfiram, and cysteamine or panthethine and their derivatives show the breakdown of L-Dopa into its biological metabolites. The present invention is intended to include any method by which the level of L-DOPA in poultry may be artificially elevated for at least 3 days prior to oviposition or during the lay cycle in order to produce eggs having a lower cholesterol and fat levels, increased protein content and a reduced ratio of saturated to unsaturated fatty acids.

The studies described above were carried out on layer hens. However, the present invention may be employed with any egg laying animal and especially those that produce eggs for human consumption. Thus, the method may be used to reduce the cholesterol and fat content and saturated/unsaturated fatty acid ratio in the eggs of geese, ducks, turkeys, quail, turtles or fish (caviar).

What is claimed is:

1. A method of altering the contents of eggs produced by poultry which comprises administering to said poultry an effective amount of L-dihydroxyphenylalanine (L-DOPA) to accomplish at least one of:

reducing the ratio of saturated to unsaturated fatty acids in said eggs;

reducing the amount of saturated fatty acids in said eggs reducing the total fat content of said eggs; and increasing the protein content of said eggs.

2. The method of claim 1 wherein said effective amount comprises between 40 and 300 mg/kg of body weight of L-DOPA per day.

3. The method of claim 2 wherein said effective amount comprises between 50 and 150 mg/kg of body weight of L-DOPA per day.

4. The method of claim 2 wherein said effective amount of L-DOPA is administered orally.

5. The method of claim 4 wherein said effective amount of L-DOPA is administered for between about 3 and about 15 days.

6. A method of altering the contents of eggs produced by poultry which comprises administering to said poultry an effective amount of a drug which elevates the level of L-DOPA in the bloodstream of said poultry, wherein said drug is not L-DOPA, to accomplish at least one of:

reducing the ratio of saturated to unsaturated fatty acids in said eggs;

reducing the amount of saturated fatty acids in said eggs reducing the total fat content of said eggs; and increasing the protein content of said eggs.

7. The method of claim 6 wherein said drug is a member selected from the group consisting of dopa decarboxylase inhibitors, dopamine beta hydroxylase inhibitors, tyrosine, phenylalanine and combinations thereof.

8. The method of claim 7 wherein said dopa decarboxylase inhibitors are selected from the group consisting of carbidopa, benserazide, and combinations thereof.

9. The method of claim 8 wherein said effective amount is about 5 to about 50 mg per kilogram of body weight per day.

10. The method of claim 8 wherein said effective amount is about 10 to about 50 mg per kilogram of body weight per day.

11. The method of claim 7, wherein said dopamine beta hydroxylase inhibitors are selected from the group consisting of fusaric acid, disulfiram, cysteamine, phosphocysteamine, pantethine, pantetheine, 3-pyridineacetic acid and 3-(3-pyridylmethoxycarbonyl)-propionic acid esters of pantethine and pantetheine, pantetheine-4'-phosphate, pharmaceutically acceptable salts thereof, and combinations thereof.

12. The method of claim 8 which comprises administering an effective amount of L-DOPA prior to the administration of said drug.

13. The method of claim 11 which comprises administration of L-DOPA prior to the administration of said drug.

14. The method of claim 7 wherein said effective amount is administered orally.

15. The method of claim 7 wherein said effective amount is administered for between about 3 and about 15 days.

16. The method of claim 1, which comprises administering to said poultry an effective amount of L-dihydroxyphenylalanine (L-DOPA) to reduce the ratio of saturated to unsaturated fatty acids in said eggs.

17. The method of claim 1, which comprises administering to said poultry an effective amount of L-dihydroxyphenylalanine (L-DOPA) to reduce the amount of saturated fatty acids in said eggs.

18. The method of claim 1, which comprises administering to said poultry an effective amount of L-dihydroxyphenylalanine (L-DOPA) to reduce the total fat content of said eggs.

19. The method of claim 1, which comprises administering to said poultry an effective amount of L-dihydroxyphenylalanine (L-DOPA) to increase the protein content of said eggs.

20. The method of claim 6 which comprises administering to said poultry an effective amount of a drug which elevates the level of L-DOPA in the bloodstream of said poultry, wherein said drug is not L-DOPA, to reduce the ratio of saturated to unsaturated fatty acids in said eggs.

21. The method of claim 6 which comprises administering to said poultry an effective amount of a drug which elevates the level of L-DOPA in the bloodstream of said poultry, wherein said drug is not L-DOPA, to reduce the amount of saturated fatty acids in said eggs.

22. The method of claim 6 which comprises administering to said poultry an effective amount of a drug which elevates the level of L-DOPA in the bloodstream of said poultry, wherein said drug is not L-DOPA, to reduce the total fat content of said eggs.

23. The method of claim 6 which comprises administering to said poultry an effective amount of a drug which elevates the level of L-DOPA in the bloodstream of said poultry, wherein said drug is not L-DOPA, to increase the protein content of said eggs.

* * * * *

UNITED STATES PATENT AND TRADEMARK OFFICE
CERTIFICATE OF CORRECTION

PATENT NO. : 5,759,567
DATED : Jun. 2, 1998
INVENTOR(S) : Albert H. Meier, John M. Wilson It is certified that error appears in the above-indentified patent and that said Letters Patent is hereby corrected as shown below:

Title page: Item "[75] Inventors:", after "John M. Wilson" please delete "Charlestown, Mass." and insert --Metairie, LA--

Signed and Sealed this

Fifth Day of January, 1999

Attest:

Attesting Officer

*Acting Commissioner of Patents and Trademarks*